United States Patent
Gaeth et al.

(10) Patent No.: US 7,709,693 B2
(45) Date of Patent: May 4, 2010

(54) TOLUENE PRODUCTION

(75) Inventors: Benjamin F. Gaeth, Pearland, TX (US); Reynaldo E. Vera, Alvin, TX (US)

(73) Assignee: Equistar Chemicals, LP, Houston, TX (US)

( * ) Notice: Subject to any disclaimer, the term of this patent is extended or adjusted under 35 U.S.C. 154(b) by 427 days.

(21) Appl. No.: 11/906,307

(22) Filed: Oct. 1, 2007

(65) Prior Publication Data

US 2009/0084668 A1    Apr. 2, 2009

(51) Int. Cl.
    *C07C 7/08*    (2006.01)
(52) U.S. Cl. .................. 585/807; 585/833; 585/854; 585/804
(58) Field of Classification Search ............. 585/804, 585/807, 833, 854
    See application file for complete search history.

(56) References Cited

U.S. PATENT DOCUMENTS

| | | | | |
|---|---|---|---|---|
| 2,381,092 | A * | 8/1945 | Wilson | 208/313 |
| 2,742,411 | A * | 4/1956 | Leary et al. | 203/46 |
| 2,768,986 | A * | 10/1956 | Lien et al. | 585/843 |
| 2,773,918 | A | 12/1956 | Stephens | 260/674 |
| 2,831,905 | A * | 4/1958 | Nelson | 585/865 |
| 3,361,664 | A | 1/1968 | Broughton et al. | 208/313 |
| 6,090,270 | A * | 7/2000 | Gildert | 208/57 |
| 2008/0194900 | A1 * | 8/2008 | Bhirud | 585/648 |

* cited by examiner

*Primary Examiner*—Tam M Nguyen
(74) *Attorney, Agent, or Firm*—Roderick W. MacDonald

(57) ABSTRACT

A method for optimizing the production of nitration grade toluene from a solvent extraction process that produces an aromatic rich extract and a saturate rich raffinate, comprising adding an effective amount of the raffinate back to the extract.

5 Claims, 2 Drawing Sheets

TOLUENE PRODUCTION

BACKGROUND OF THE INVENTION

1. Field of the Invention

This invention relates to the production of a nitration grade toluene product. More particularly, this invention relates to the production of a nitration grade toluene product from the process of thermal cracking hydrocarbons.

2. Description of the Prior Art

Thermal cracking of hydrocarbons is a petrochemical process that is widely used to produce olefins such as ethylene, propylene, butenes, butadiene, and aromatics such as benzene, toluene, and xylenes. In an olefin production plant, a hydrocarbonaceous feedstock such as ethane, naphtha, gas oil, or other fractions of whole crude oil is mixed with steam which serves as a diluent to keep the hydrocarbon molecules separated.

This mixture, after preheating, is subjected to hydrocarbon thermal cracking using elevated temperatures (1,450 to 1,550 degrees Fahrenheit or F.) in a pyrolysis furnace (steam cracker or cracker). This thermal cracking is carried out without the aid of any catalyst.

The cracked product effluent of the pyrolysis furnace (furnace) contains hot, gaseous hydrocarbons of great variety (from 1 to 35 carbon atoms per molecule, or C1 to C35 inclusive, both saturated and unsaturated). This product contains aliphatics (alkanes and alkenes), alicyclics (cyclanes, cyclenes, and cyclodienes), aromatics, and molecular hydrogen (hydrogen).

This furnace product is then subjected to further processing to produce, as products of the olefin plant, various, separate and individual product streams such as hydrogen, ethylene, propylene, and fuel oil. After the separation of these individual streams, the remaining pyrolysis gasoline contains essentially C4 hydrocarbons and heavier. This remainder is fed to a debutanizer wherein a crude C4 stream is separated as overhead while a C5 and heavier stream is removed as a bottoms product.

The C4 stream can contain varying amounts of n-butane, isobutane, 1-butene, 2-butenes (both cis and trans isomers), isobutylene, acetylenes, and diolefins such as butadiene (both cis and trans isomers).

The C5 and heavier stream contains primarily (in major proportion, greater than 50% by weight) C6 through C8 hydrocarbons, both aromatic and non-aromatic (alkanes and alkenes). Aromatics are separated from this stream by way of a solvent extraction process, and the aromatics in the extract are themselves separated to recover individual plant product streams such as a benzene product, a toluene product, and the like. The non-aromatics are typically passed to the gasoline pool.

There are several marketable grades of toluene product that can be recovered from the aromatic rich extract that is recovered from the solvent extraction process. The grades of toluene product are "commercial" which contains at least 95 weight percent (wt %) toluene, "nitration grade" which contains at least 98.5 wt % toluene, and "TDI grade" which contains at least 99.9 wt % toluene, all wt % based on the total weight of the product.

This invention is directed toward producing an optimum amount of nitration grade toluene product from the aromatic (primarily benzene and toluene) rich extract of a solvent extraction.

SUMMARY OF THE INVENTION

Pursuant to this invention, the quantity of nitration grade toluene product recovered from the aforesaid extract is optimized by first recovering benzene from the extract followed by blending with the remaining extract an effective amount of raffinate that was generated by the solvent extraction process.

This invention is particularly effective if the aforesaid blending takes place upstream of the typical benzene splitter column that is conventionally employed upstream of the distillation column that produces the nitration grade toluene product of the plant.

In this description, a distinction is made between a distillation column and a splitter column and that is a splitter column makes a cleaner (finer, narrower) cut of the desired product than does a distillation column. For example, with a benzene distillation column whose primary goal is to remove a benzene stream from a mixture of hydrocarbons containing benzene, more benzene, on a comparative weight basis, will be left in the bottoms (non-benzene) product of that column than would be left in the bottoms (non-benzene) product of a benzene stripper column whose primary goal is the same. Put another way, the benzene splitter column will come nearer to recovering all the benzene present in that column as a separate overhead product than would a benzene distillation column. This is accomplished in one way, as an example, by employing more distillation trays in a splitter column than in a distillation column.

DETAILED DESCRIPTION OF THE INVENTION

Figure 1:
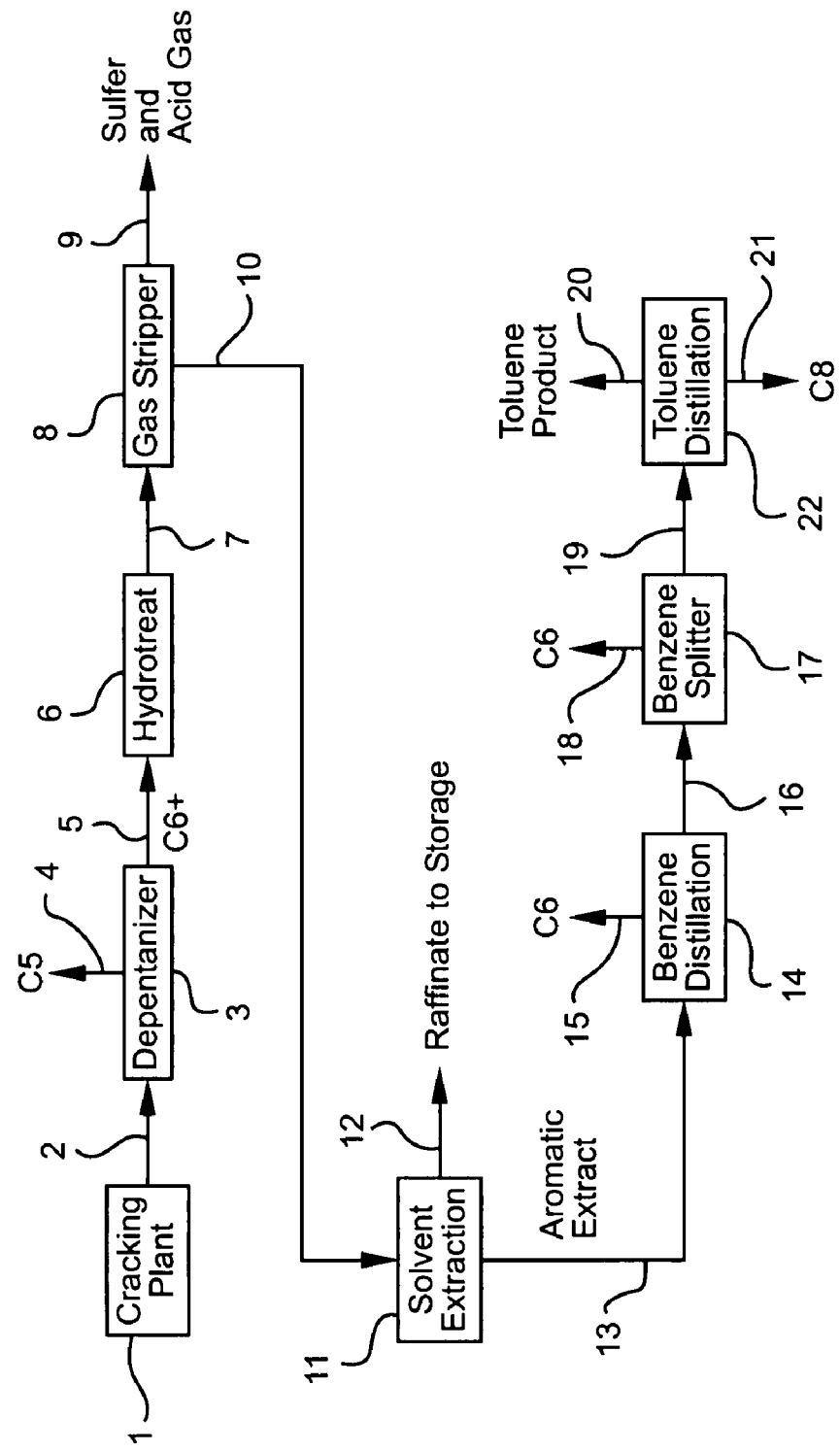
FIG. 1 is a simplified flow diagram of a typical thermal cracking plant integrated with the C6 and heavier section of its hydrocarbons processing unit.

FIG. 1 shows a thermal cracking plant 1. In plant 1 hydrogen, ethylene, propylene, fuel oil, pyrolysis gasoline and a C4 stream (not shown) have been separated from the cracked product stream of the pyrolysis furnaces in plant 1, thereby leaving a C5 and heavier stream 2 to which this invention is directed.

Stream 2 is typically processed in a de-pentanizing column 3 from which is taken a C5 stream 4 which is processed (not shown) elsewhere in the hydrocarbons processing unit.

The remainder of stream 2, containing primarily C6 and heavier hydrocarbons, is removed as stream 5 and passed into a hydrotreating unit 6 wherein alkenes and thiols are selectively saturated to alkanes thereby producing a stream 7 that is primarily composed of aromatics and saturated non-aromatics.

Stream 7 is passed to a degassing tower 8 for the removal from stream 7 of sulfur and acid gas that was formed in hydrotreaters 6. The remainder of stream 7 forms stream 10. Stream 10 is composed primarily of C6 and C7 hydrocarbons both aromatic and alkane with very minor amounts, from about 0.3 to about 4 wt % based on the total weight of stream 10, of C5 and C8 hydrocarbons (aromatic and non-aromatic).

Stream 10 is passed to a conventional solvent extraction process which uses a solvent that preferentially removes aromatic hydrocarbons from stream 10 to form an extract 13, and leaves the saturates (C6 and C7 non-aromatics) in a separate raffinate stream 12 together with minor amounts, from about 0.3 to about 13.0 wt % based on the total weight of stream 12, of toluene.

The solvent extraction of aromatics can employ various solvents such as sulfolane, liquid SO2, N-methyl pyrrolidone, and glycols such as diethylene glycol and tetraethylene glycol. Aromatic extraction by glycols, for example, is based on the electrophilic nature of oxygen causing dipoles which exist along the glycol molecule. These dipoles give glycols their affinity for water which is highly polar and aromatics which are non-polar. It would seem that non-polar aromatics would have no attraction to polar glycol molecules, but the pi-electrons of a benzene ring are delocalized over the entire ring, and this allows these electrons freely to travel to each of the six carbons of the benzene ring. Polar solvents interact preferentially with the mobile pi-electrons in the benzene ring of aromatics. This allows the glycol molecule to assume the physical configuration of a bent horseshoe, which brings its positive sites closer to the outside diameter of a benzene ring, the glycol molecule thus essentially surrounds the aromatic molecule, and forms a solvent phase containing primarily aromatic molecules. The solvent molecules reject the non-aromatic molecules. The non-aromatics are transported to the hydrocarbon/solvent interface, and are thereby rejected to the raffinate phase. Solvent extraction is well known in the art, and further description is not needed to inform the art. This process is fully and completely disclosed in detail in U.S. Pat. Nos. 2,773,918 and 3,361,664.

Raffinate stream 12 is rich in non-aromatic hydrocarbons, and is normally sent to storage for subsequent processing outside the boundaries of the plant.

The aromatic rich extract/solvent complex is processed in unit 11 for recovery of the solvent for re-use in the solvent extraction step thereby leaving an aromatic rich extract stream 13 which contains primarily benzene and toluene and very minor amounts, from about 0.1 to about 0.2 wt % based on the total weight of stream 13, of C6, C7, and C8 hydrocarbons (aromatic and non-aromatic).

Extract stream 13 is introduced into a benzene distillation column 14, and a benzene stream 15 is recovered overhead therefrom. Stream 15 is marketed as a commercial product of the plant. This leaves a toluene rich stream 16 that is passed to a benzene splitter column 17 for the removal by way of stream 18 of yet more C6 hydrocarbons, i.e., hydrocarbons lighter boiling than toluene. Stream 18 is composed primarily of C6's (aromatic and non-aromatic) and is typically passed to the gasoline pool. The toluene rich bottoms stream 19 of splitter 17 is passed to a toluene distillation tower 22 for recovery by way of stream 20 of the toluene product of the plant.

In this invention stream 20 is the desired nitration grade toluene product of the overall plant.

Any remaining C8 hydrocarbons such as xylenes are removed by way of stream 21 and are normally passed to the gasoline pool.

Figure 2:
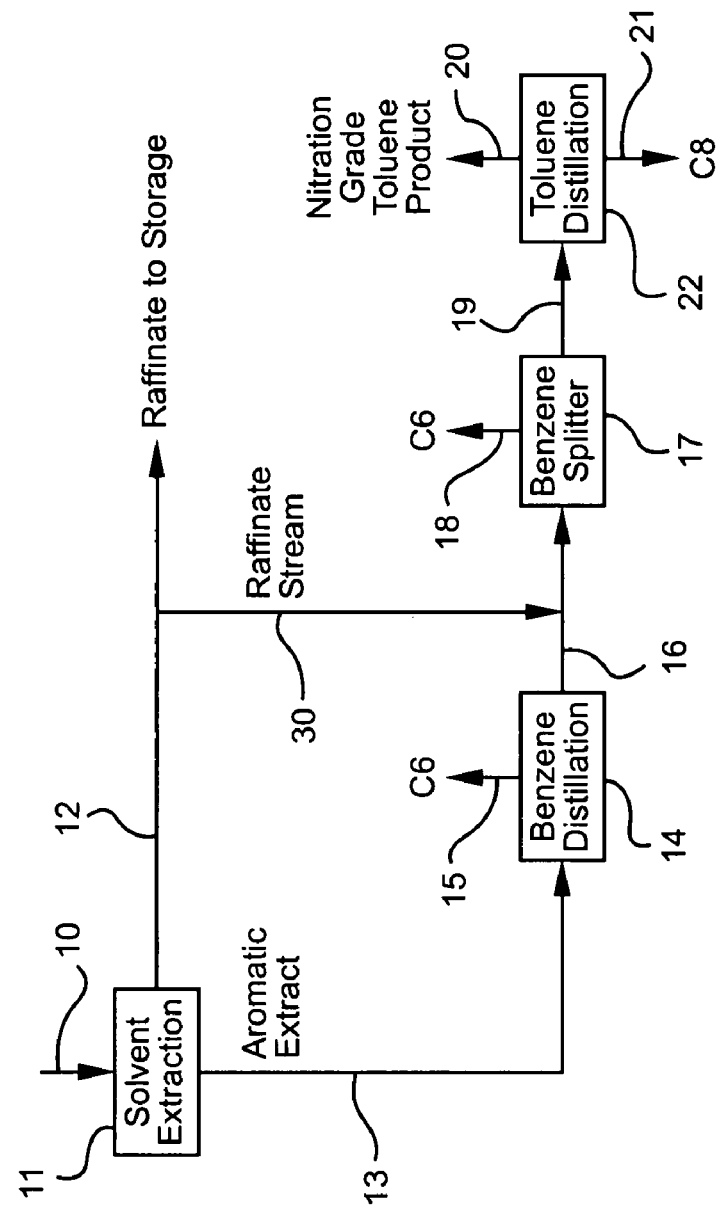
FIG. 2 shows a modification of the C6 and heavier section of FIG. 1 in accordance with this invention.

FIG. 2 shows the process of FIG. 1 modified in a manner pursuant to this invention.

In FIG. 2 an effective amount of raffinate 12 is passed by way of stream 30 to be blended with extract stream 16. The process of this invention is effectively preferably carried out by adding stream 30 to the extract stream upstream of benzene splitter 17 so that C6 hydrocarbons in stream 30 that are lighter boiling than toluene can be removed before the toluene distillation step 22 is performed.

Adding raffinate that has just been separated from the extract back to that extract is counter intuitive in the art, and goes against the teachings of the art, but is surprisingly effective in the operation of this invention.

Raffinate 12 can contain from about 50 to about 55 wt % hexanes, from about 35 to about 40 wt % heptanes, and from about 7 to about 8 wt % toluene, the remainder, if any, being essentially C8 aromatics (xylenes) and benzene.

Pursuant to this invention, an effective amount of raffinate can be employed along with extract stream 16 to produce an amount of nitration grade toluene product 20 that is optimum for the particular operating characteristics of the plant in which this invention is practiced.

The effective amount of raffinate added to extract stream 16 can vary widely depending on the particular operating characteristics of the plant in which this invention is employed, but can, for example, vary from about 2 to about 4 wt % of stream 16, based on the total weight of that stream 16.

EXAMPLE

In the process of FIG. 2, steam 16 can contain about 90 wt % toluene, the remainder being C6 and C8 hydrocarbons, both aromatic and non-aromatic.

Stream 30, as added to stream 16, can contain about 53% hexanes, about 38 wt % heptanes, about 7 wt % toluene, less than about 2 wt % xylenes, and less than about 1 wt % benzene, all wt % based on the total weight of the stream.

Stream 30 is mixed with stream 16 in the amount of about 3 wt % based on the total weight of stream 30.

The combined stream formed from streams 16 and 30 aforesaid is passed into benzene splitter column 17 which is operated in a manner to produce a C6 stream 18 containing essentially only C6 aromatics and non-aromatics, and a separate stream 19 containing about 95 wt % toluene, the remainder being essentially only C7 and C8 hydrocarbons, both aromatic and non-aromatic.

The operation of column 17 also produces a nitration grade toluene plant product 20 which contains at least about 98.5 wt % toluene, the remainder being C7 and C8 hydrocarbons, both aromatic and non-aromatic.

We claim:

1. In a method for optimizing the production of nitration grade toluene product from a feed containing primarily C6 and C7 aromatic and non-aromatic hydrocarbons including benzene and toluene, said method using a solvent extraction process that forms an extract stream containing primarily benzene and toluene and a separate raffinate stream containing primarily C6 and C7 non-aromatic hydrocarbons and toluene, said extract stream being subjected to a benzene distillation step to remove benzene from said extract stream, said benzene distillation step being followed by a benzene splitter step to remove additional C6 hydrocarbons from said extract stream, said benzene splitter step being followed by a toluene distillation step from which a toluene product is recovered, the improvement comprising adding a portion of said raffinate stream to said extract stream downstream of said benzene distillation step, whereby an optimized volume of nitration grade toluene product is formed.

2. The method of claim 1 wherein said raffinate is added to said extract stream upstream of said benzene splitter step.

3. The method of claim 2 wherein in said benzene splitter step hydrocarbons lighter than toluene are removed from said portion of said raffinate stream that was added to said extract stream upstream of said benzene splitter step.

4. The method of claim 1 wherein said portion of said raffinate added to said extract stream is from about 2 to about 4 wt % based on the total weight of said extract stream.

5. The method of claim 1 wherein said raffinate added to said extract stream contains from about 50 to about 55 wt % hexanes, from about 35 to about 40 wt % heptanes, and from about 7 to about 8 wt % toluene, with the remainder, if any, being xylenes and benzene, all wt % being based on the total weight of said added raffinate.

* * * * *